United States Patent
Poulo

(10) Patent No.: US 10,470,824 B2
(45) Date of Patent: Nov. 12, 2019

(54) IMAGING APPARATUS AND INTERVENTIONAL INSTRUMENT EVENT MAPPER

(71) Applicant: BK Medical Holding Company, Inc., Peabody, MA (US)

(72) Inventor: Louis Poulo, Andover, MA (US)

(73) Assignee: BK Medical Holding Company, Peabody, MA (US)

( * ) Notice: Subject to any disclaimer, the term of this patent is extended or adjusted under 35 U.S.C. 154(b) by 587 days.

(21) Appl. No.: 15/112,762

(22) PCT Filed: Jan. 22, 2014

(86) PCT No.: PCT/IB2014/058473
§ 371 (c)(1),
(2) Date: Jul. 20, 2016

(87) PCT Pub. No.: WO2015/110866
PCT Pub. Date: Jul. 30, 2015

(65) Prior Publication Data
US 2016/0338779 A1    Nov. 24, 2016

(51) Int. Cl.
*A61B 34/20*    (2016.01)
*A61B 6/12*    (2006.01)
(Continued)

(52) U.S. Cl.
CPC ............. *A61B 34/20* (2016.02); *A61B 5/055* (2013.01); *A61B 5/061* (2013.01); *A61B 6/032* (2013.01);
(Continued)

(58) Field of Classification Search
CPC .............................................. A61B 2034/2055
See application file for complete search history.

(56) References Cited

U.S. PATENT DOCUMENTS

2009/0234223 A1    9/2009    Onoda et al.
2013/0211243 A1    8/2013    Zhang et al.
(Continued)

FOREIGN PATENT DOCUMENTS

CN    101569545 A    11/2009
CN    102791225 A    7/2011
(Continued)

OTHER PUBLICATIONS

International Search Report for PCT/IB2014/058743 published as WO2015/110866 A1 dated Jul. 30, 2015.

*Primary Examiner* — Omkar A Deodhar
(74) *Attorney, Agent, or Firm* — Anthony M. Del Zoppo, III; Daugherty & Del Zoppo Co., L.P.A.

(57) ABSTRACT

A system (102) includes an interventional instrument (104) and an imaging apparatus (106). The interventional instrument includes an interventional instrument event tracking transmitter (116) that transmits an interventional instrument event signal in response to a predetermined interventional instrument event by interventional instrument in connection with an interventional procedure for a region of interest of a subject. The imaging apparatus (106) includes an imager (132) that generates image of the region of interest of the subject. The imaging apparatus (106) further includes a receiver (126) that receives the interventional instrument event signal. The imaging apparatus (106) further includes an instrument event mapper (128) that maps the predetermined interventional instrument event to the image based on the received interventional instrument event signal.

20 Claims, 4 Drawing Sheets

(51) Int. Cl.
  *A61B 8/08* (2006.01)
  *A61B 5/055* (2006.01)
  *A61B 10/02* (2006.01)
  *A61B 6/03* (2006.01)
  *A61M 25/09* (2006.01)
  *A61B 5/06* (2006.01)
  *A61B 8/00* (2006.01)
  *A61B 90/00* (2016.01)

(52) U.S. Cl.
  CPC .............. *A61B 6/12* (2013.01); *A61B 8/0841* (2013.01); *A61B 10/0233* (2013.01); *A61M 25/09* (2013.01); *A61B 5/06* (2013.01); *A61B 8/4416* (2013.01); *A61B 8/4444* (2013.01); *A61B 8/468* (2013.01); *A61B 2010/0208* (2013.01); *A61B 2034/2063* (2016.02); *A61B 2034/2065* (2016.02); *A61B 2090/374* (2016.02); *A61B 2090/376* (2016.02); *A61B 2090/378* (2016.02)

(56) References Cited

U.S. PATENT DOCUMENTS

2013/0289393 A1* 10/2013 Kruecker ............. A61B 8/0841
  600/424
2013/0338477 A1   12/2013 Glossop et al.

FOREIGN PATENT DOCUMENTS

| CN | 102905613 A | 8/2013 |
| EP | 2478855 A1 | 7/2012 |
| WO | 2012/098483 A1 | 7/2012 |

* cited by examiner

IMAGING APPARATUS AND INTERVENTIONAL INSTRUMENT EVENT MAPPER

RELATED APPLICATION

This application is a national filing of PCT application Serial No. PCT/IB2014/058473, filed Jan. 22, 2014, published as WO2015/110866 on Jul. 30, 2015. This application claims priority to PCT application Serial No. PCT/IB2014/058473, published as WO2015/110866 on Jul. 30, 2015.

TECHNICAL FIELD

The following generally relates to imaging, and more particularly to an imaging apparatus with an interventional instrument event mapper, and is described with particular application to ultrasound (US) imaging; however, the following is also amenable to other imaging modalities such as magnetic resonance imaging (MRI), computed tomography (CT), X-ray, etc.

BACKGROUND

An ultrasound imaging apparatus has included a transducer array that transmits an ultrasound beam into an examination field of view. As the beam traverses structure (e.g., an object or subject, an instrument, etc.) in the field of view, sub-portions of the beam are attenuated, scattered, and/or reflected off the structure, with some of the reflections (echoes) traversing back towards the transducer array. The transducer array receives and processes the echoes, and generates one or more images of the subject or object and/or instrument.

Ultrasound imaging has been used to guide biopsy procedures. Ultrasound imaging-guided biopsy procedures have been performed with a biopsy needle attached to the ultrasound probe (or otherwise guided, such as free-hand) so that the tip of the biopsy needle is in the imaging field of view (FOV). The ultrasound imaging apparatus is used to generate images of the field of view and the needle, and the images are used by the operator to move the needle to the tissue of interest so that a tissue sample(s) can be taken at a desired location(s) of the tissue of interest and acquire the sample.

Once the biopsy is finished, the needle is removed. The images, if saved, can later be used to visualize needle entry, movement of the needle to the tissue of interest, the needle tip at the tissue of interest, and/or removal of the needle. However, such information does not indicate the moment in time at which a biopsy was performed. As such, it may not be clear when and where the biopsy was actually performed. Furthermore, there is no reference point which can be used to guide and/or compare a subsequent biopsy of the same tissue of interest.

SUMMARY

Aspects of the application address the above matters, and others.

In one aspect, a system includes an interventional instrument and an imaging apparatus. The interventional instrument includes an interventional instrument event tracking transmitter that transmits an interventional instrument event signal in response to a predetermined interventional instrument event by interventional instrument in connection with an interventional procedure for a region of interest of a subject. The imaging apparatus includes an imager that generates image of the region of interest of the subject. The imaging apparatus further includes a receiver that receives the interventional instrument event signal. The imaging apparatus further includes an instrument event mapper that maps the predetermined interventional instrument event to the image based on the received interventional instrument event signal.

In another aspect, a method includes receiving, in electronic format, a signal indicating an occurrence of an action of an interventional instrument at region of interest in a subject at a point in time during an interventional procedure. The method further includes mapping the signal to an image acquired at the point in time during the interventional procedure, generating a mapping signal. The method further includes storing the mapping signal in computer memory.

In another aspect, a system includes means for an interventional procedure. The system further includes means for acquiring image data for the interventional procedure. The system further includes a receiver that receives a signal transmitted by the means for performing the interventional procedure. The signal indicates a predetermined interventional procedure event occurred. The system further includes an instrument event mapper that generates a mapping between the signal and a corresponding image generated by the means for acquiring image data.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
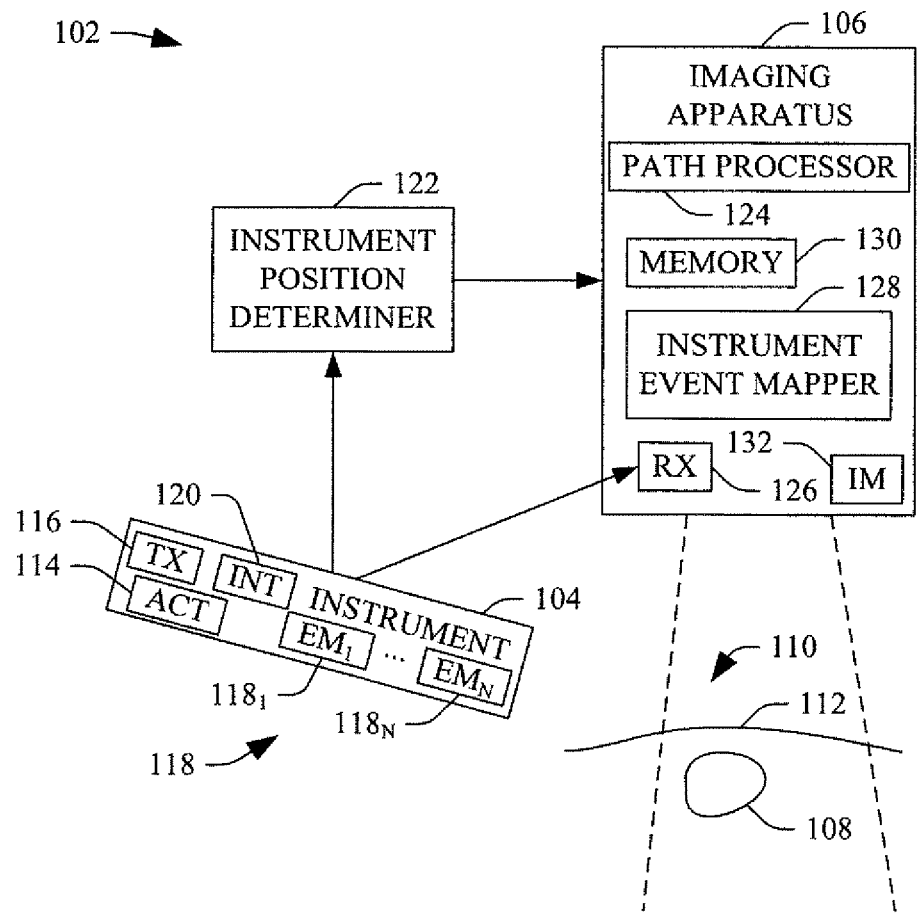
FIG. 1 schematically illustrates an imaging apparatus in connection with an interventional instrument.

FIG. 1 schematically illustrates a system 102, which includes, at least, an interventional instrument (instrument) 104 and at least one (only one shown in FIG. 1) imaging apparatus 106.

The instrument 104, for example, is an appropriate interventional instrument for an imaging-guided medical procedure. For example, where the imaging-guided procedure is an aspiration biopsy, the instrument 104 may include a needle, a guide wire, a lumen, and/or other device. In this example, generally, the instrument 104 can be any device that can obtain a sample of tissue, fluid, etc., that includes cells of interest, such as cells suspected to include cancer, tumor, etc. cells. Such medical procedures have been performed by a cytopathologist, a surgeon, an interventional radiologist, a clinician with training in performing such biopsies (e.g., under x-ray, ultrasound, etc. guidance), and/or otherwise.

Figure 2:
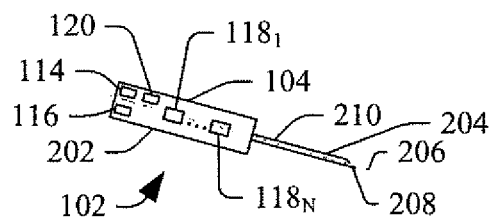
FIG. 2 schematically illustrates an example of the interventional instrument of FIG. 1.

For explanatory purposes, the instrument 104 is described as including a biopsy needle. A non-limiting example of such an instrument is schematically shown in FIG. 2. In FIG. 2, the instrument 104 includes a handle or support 202, an elongate needle 204, and a long axis 206. The elongate needle 204 includes a tip 208 and a shaft 210, which is supported by the support 202. Returning to FIG. 1 and with continuing reference to FIG. 2, at least the tip 208 of the needle 204, for the illustrated procedure, is to be navigated or moved into an object or region of interest 108 (e.g., tissue, fluid, etc.) of a subject 110 having a surface 112. In this example, the needle 204, under guidance of images generated by the imaging apparatus 106, is passed through the surface 112 and moved to the object of interest 108.

With continued reference to FIGS. 1 and 2, the instrument 104 further includes an actuator 114 (ACT). The actuator 114, for example, is a physical mechanical switch or the like, which is actuated by a user (e.g., a robot, a human, etc.) and/or the instrument 104. For the former, for example, the user may push button, pivot a lever, slide an element, etc. to actuate the actuator 114. For the later, for example, in the context of a biopsy instrument, the mechanism which invokes acquisition of a biopsy sample may actuate the actuator 114. The instrument 104 also includes an event tracking transmitter (transmitter) 116 (TX). The transmitter 116, in response to actuation by the actuator 114, generates and transmits an interventional instrument event signal, which, as described herein, can be used to indicate that the instrument 104 has performed an action (e.g., acquired a sample).

The illustrated instrument 104 further includes N emitters, $118_1$ ($EM_1$), ..., $118_N$ ($EM_N$) (collectively referred to herein as emitters 118), where N is a positive integer equal to or greater than one (1). The emitters 118, in general, include a tracking device that provides information which can be used to determine the spatial location and/or the orientation of the tracking device and hence the instrument 104. This information can be used, for example, to identify the location of the instrument 104 in an image generated by the imaging apparatus 106 where the instrument 104 is not visible in the images. In such instances, visual indicia (e.g., an arrow, a line, etc.) can be placed on the image to provide an indication of where the instrument 104 is located. An external tracking system can additionally or alternatively be used.

The instrument 104 further includes an interface 120 (INT). The interface 120 can include an electro-mechanical interface configured to receive a complementary physical connector of a cable or the like. Additionally or alternatively, the interface 120 can include a wireless interface. In one instance, the signal transmitted from the transmitter 116 is conveyed off the instrument 104 through the interface 120. Alternatively, the transmitter 120 directly transmits the signal off the instrument 104. The interface 120 also is used to convey the signals emitted from the emitters 118 off the instrument 104. The interface 120 may be a single interface, include multiple sub-interfaces (e.g., one for the transmitter 116 and one for the emitters 118), or comprise two separate and distinct interfaces (e.g., one for the transmitter 116 and one for the emitters 118).

An instrument position determiner 122 receives the signals from the emitters 118 and determines the location and/or orientation of the emitters. Examples of suitable position determiner systems are described in U.S. patent application Ser. No. 12/703,706, filed Feb. 10, 2010, and entitled "Ultrasound Systems Incorporating Position Sensors and Associated Method," which is incorporated herein by reference in its entirety, and U.S. patent application Ser. No. 12/775,403, filed May 6, 2010, and entitled "Freehand Ultrasound Imaging Systems and Methods for Guiding Elongate Instruments," which is incorporated herein by reference in its entirety. Other approaches are also contemplated herein. As disclosed at least in these references, an emitter, a sensor, and/or a transmitter can also be affixed to an imager of the image apparatus 106.

The imaging apparatus 106 can be ultrasound (US), magnetic resonance (MR), computed tomography (CT), and/or other imaging apparatus, e.g., that generates imaging data which can be used to visually observe the instrument 104 during an imaging-guided procedure such as a biopsy, a surgical, and/or other procedure. That is, an image generated at a particular time point will visually show the instrument 104 and hence its location at that time point, if the instrument 104 is visible at the time point. In a variation, the system 102 can include more than one imaging apparatus. An example of such a system is described in international application serial number PCT/US13/72154, filed on Nov. 27, 2013, and entitled "Multi-Imaging Modality Navigation System," which is incorporated by reference in its entirety herein.

The imaging apparatus 106 further includes a receiver (RX) 126 that receives the signal generated and transmitted by the transmitter 116. An instrument event mapper 128, in response to the receiver 126 receiving the signal, identifies at least the current image generated by the imaging instrument 106 and also, optionally, as in the illustrated embodiment, the location and the orientation of a tip of the instrument 104 from the signal which is from the instrument position determiner 122. This may include adding indicia to the image, setting a bit(s) in a register, recording a frame number and/or acquisition time, etc. The indicia, in one instance, indicates the time at which the signal transmitter 108 was actuated, the image generated at the time the signal transmitter 108 was actuated, and/or other information that maps an event of the instrument 104 to the imaging data of the imaging apparatus 106.

The mapping indicia can be included in the imaging data file, for example, in a header and/or other field of the data file that includes the imaging data. In this manner, the moment in time at which the event occurred is part of the imaging data. In another instance, the indicia can be included in a separate file, which is correlated, associated, mapped, etc. to the imaging data file. In this manner, the image at which the actuator 108 was actuated can be later retrieved. Such a relationship, for example, can be time based from the beginning of the imaging procedure and/or other reference point, based on an absolute time, etc. In one instance, this provides a reference, which can be used to guidance a subsequent procedure. The indicia, the imaging data file, the separate file and/or other information can be stored in a memory 130 and/or other memory, which can be local to the imaging apparatus and/or external and remote from the imaging apparatus 106. The imaging apparatus further includes an imager (IM) 132 which acquires the images.

It is to be appreciated that the instrument event mapper 128 can be implemented via one or more computer processors (e.g., a microprocessor, a control processing unit, a controller, etc.) executing one or more computer readable instructions encoded or embodied on computer readable storage medium (which excludes transitory medium), such as physical computer memory, which causes the one or more computer processors to carry out the various acts and/or other functions and/or acts. Additionally or alternatively, the one or more computer processors can execute instructions carried by transitory medium such as a signal or carrier wave.

FIGS. 3, 4, 5, and 6 illustrate examples of the imaging system 206 in which the imaging apparatus 106 includes an US imaging device. The instrument 104 is not visible, not installed, etc. in FIGS. 3, 4, and 5. Furthermore, the path processor 124, the receiver 126, the instrument event mapper 128 and the memory 130 are not shown for sake of clarity.

Figure 3:
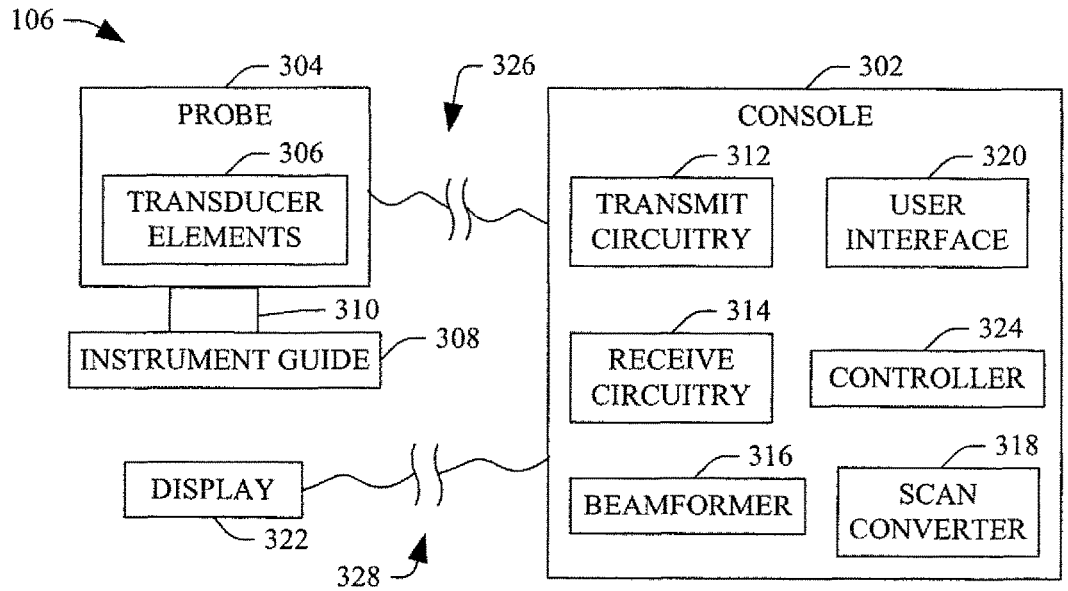
FIGS. 3, 4, 5 and 6 schematically illustrate examples of the imaging apparatus of FIG. 1.

In FIG. 3, the imaging system 106 includes a console 302 and a separate US transducer probe 304 that interfaces therewith. The ultrasound transducer probe 304 includes a transducer array with a plurality of transducer elements 306. The transducer array can be linear, curved, and/or otherwise shaped, fully populated, sparse and/or a combination thereof, etc. The transducer elements 306 can be operated in 2D and/or 3D mode. The transducer elements 306 transmit ultrasound signals and receive echo signals. An instrument guide 308, such as a biopsy needle guide, is affixed to the US transducer probe 304 through a coupling 310 such as a bracket, clamp, etc. In one instance, the instrument 104 (FIG. 1) is supported in the instrument guide 308 in a retracted position until a target tissue of interest is located with the US transducer probe 304 as described herein. Then, the needle is advanced to acquire the sample of the target tissue of interest.

Transmit circuitry 312 selectively actuates or excites one or more of the transducer elements 306. More particularly, the transmit circuitry 312 generates a set of pulses (or a pulsed signal) that are conveyed to the transducer elements 306. The set of pulses actuates a set of the transducer elements 306, causing the transducer elements 306 to transmit ultrasound signals into an examination or scan field of view. Receive circuitry 314 receives a set of echoes (or echo signals) generated in response to the transmitted ultrasound signals. The echoes, generally, are a result of the interaction between the emitted ultrasound signals and the object (e.g., flowing blood cells, organ cells, etc.) in the scan field of view. The receive circuit 314 may be configured for spatial compounding, filtering (e.g., FIR and/or IIR), and/or other echo processing.

A beamformer 316 processes the received echoes. In B-mode, this includes applying time delays and weights to the echoes and summing the delayed and weighted echoes. A scan converter 318 scan converts the data for display, e.g., by converting the beamformed data to the coordinate system of a display or display region used to visually present the resulting data. A user interface (UI) 320 include one or more input devices (e.g., a button, a knob, a slider, etc., touchscreen and/or physical mechanical device) and/or one or more output devices (e.g., a liquid crystal display, a light emitting diode, etc.), which allows for interaction between with the system 106. A display 322 visually displays the US imaging data. A controller 324 controls the various components of the system 106. For example, such control may include actuating or exciting individual or groups of transducer elements of the transducer array 202 for B-mode, C-plane, etc.

The US probe 304 and the display 322 are physically separate electromechanical components with respect to the console 302. The US probe 304 and the display 322 communicate with the console 302 through communications paths 326 and 328. The communications paths 326 and 328 can be wired (e.g., a physical cable and connectors) and/or wireless.

Figure 4:
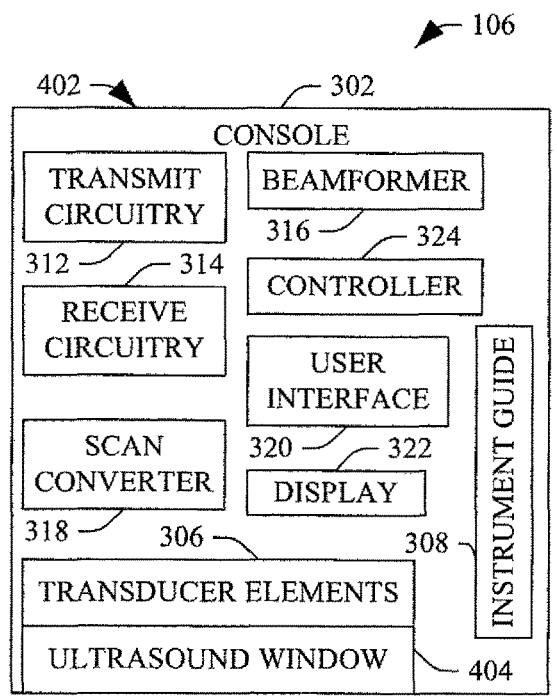

FIG. 4 illustrates a variation of the US imaging system 106. In this example, the console 302 includes a single housing 402. The single housing 402 houses and physically supports the transducer elements 306, the instrument guide 308, the transmit circuitry 312, the receive circuitry 314, the beamformer 316, the scan converter 318 and the controller 324, all of which are inside the single housing 402, which is the physical mechanical casing of the console. The user interface 320 and/or the display 322 can be part of the housing 402. For example, the display 322, in one instance, is a sub-portion of one of the sides of the housing 402. The user interface 320 may include physical mechanical controls at other locations on the housing 402. An ultrasound window 404 is also part of or integrated with the console 302. In this instance, the transducer elements 204 are disposed in the housing 402 behind the ultrasound window 404 and emit signals and receive echoes there through.

In FIG. 4, the US imaging system 106 is a hand-held ultrasound apparatus, which uses internally located power, e.g., from a power source such as a battery, a capacitor, etc. to power the components therein, and/or power from an external power source. An example of a hand-held device is described in U.S. Pat. No. 7,699,776 to Walker et al., entitled "Intuitive Ultrasonic Imaging System and Related Method Thereof," and filed on Mar. 6, 2003, which is incorporated herein in its entirety by reference. An example of hand-held ultrasound apparatus with an internal instrument guide is described in Ser. No. 13/017,344 to O'Conner, entitled "Ultrasound imaging apparatus," and filed on Jan. 31, 2011, and an example with an external instrument guide is described in U.S. Pat. No. 8,226,562 to Pelissier, entitled "Hand-Held Ultrasound System Having Sterile Enclosure," and filed on Aug. 7, 2008, both of which are incorporated herein in their entirety by reference.

Figure 5:
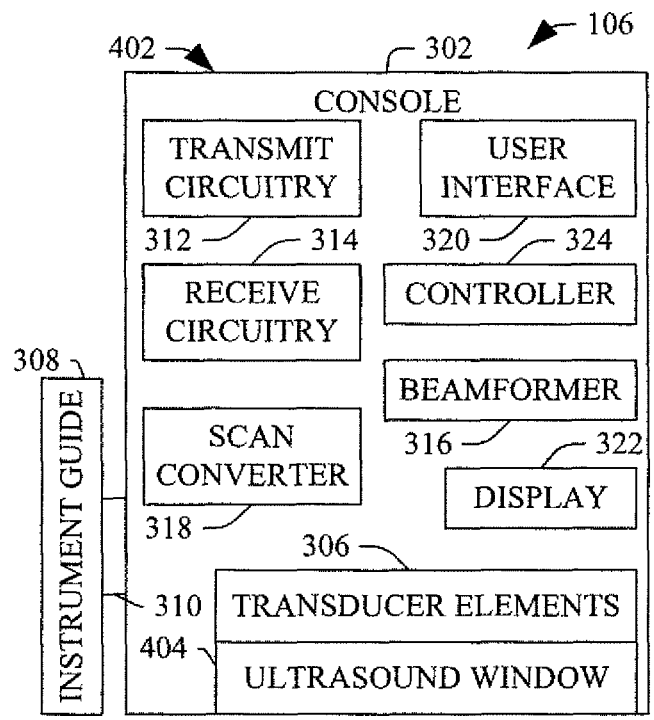
Figure 6:
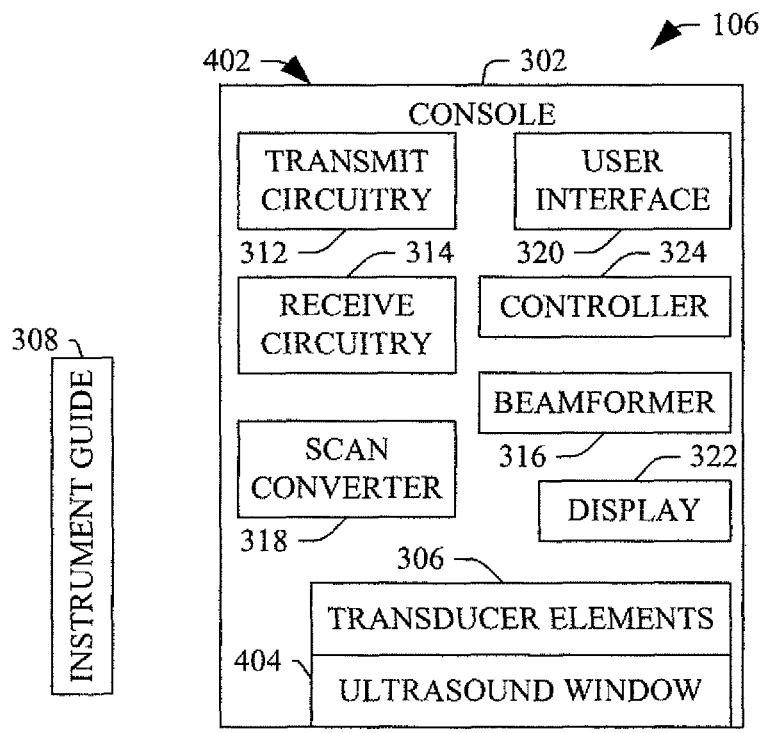

FIG. 5 illustrates a variation of FIG. 4 in which the instrument guide 308 is disposed outside of the single housing 402 and affixed thereto through the coupling 310. FIG. 6 illustrates a variation of FIGS. 4 and 5 in which the instrument guide 308 physically separate from the single housing 402. In yet another variation, the instrument guide 308 is omitted and the instrument 104 (FIG. 1) is operated free hand by the user, with a robot, and/or otherwise.

Generally, the system described herein incorporates an instrument (such as a biopsy needle system which generates a signal for communicating a time at which an event (e.g., a tissue sample) is performed), an imaging system (e.g., used for real time guidance during a procedure and which shows the location and orientation of the biopsy needle), a mechanism for receiving the signal, and a mechanism (e.g., in the imaging system) to flag, record, and optionally process, the image of the instrument and direction at the time of the event occurred. In one instance, this defines the location and orientation of the instrument at which the event occurred, which is then available on a permanent record. As such, this provides an approach to record the locations of events on the imaging record during an imaging guided procedure using the instrument, allowing future reference for use in guidance and/or diagnostics.

Figure 7:
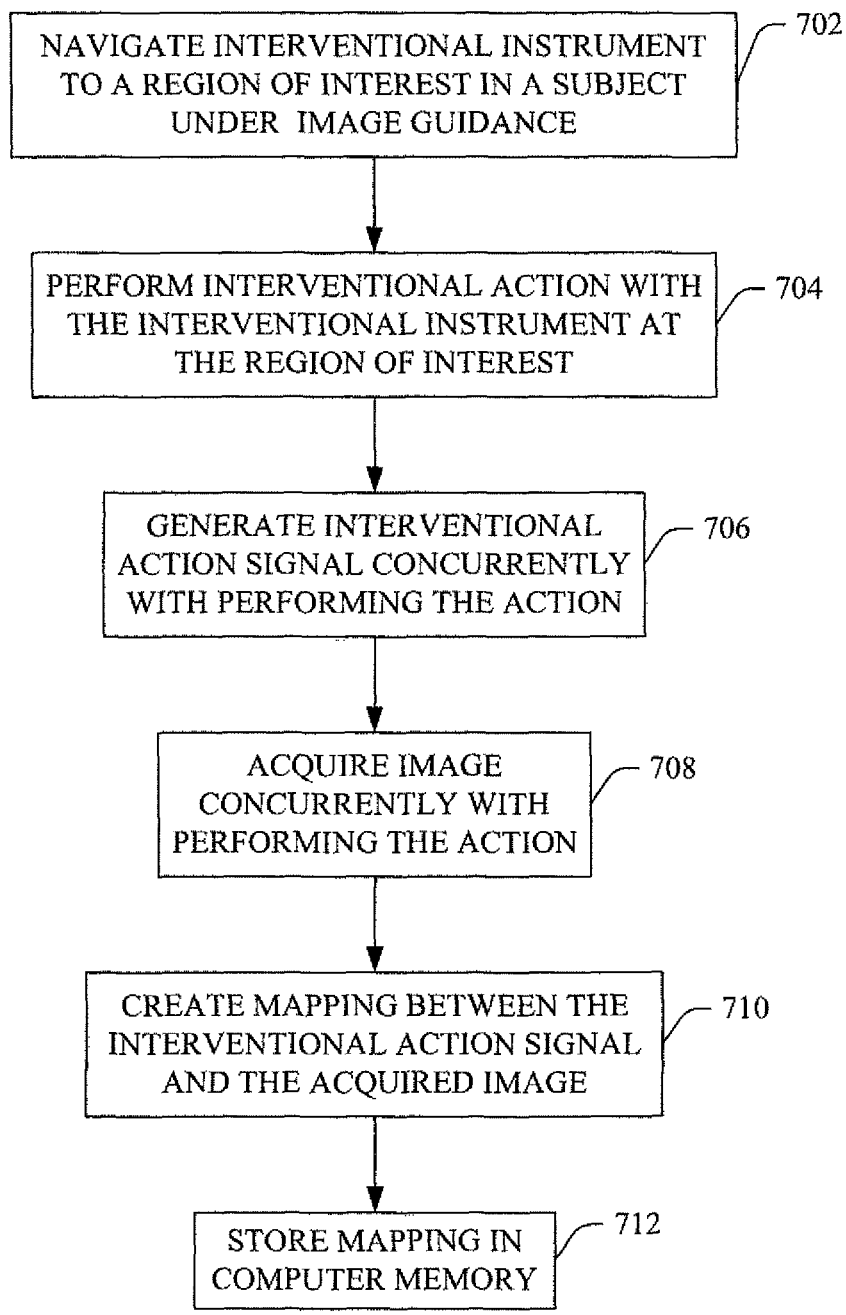
FIG. 7 illustrates an example method for recording a location and an orientation of an interventional instrument at a point in time of an interventional event in connection with an image of the interventional instrument at the point in time.

FIG. 7 illustrates an example method for recording a location and an orientation of an interventional instrument at a point in time of a predetermined interventional event.

It is to be understood that the following acts are provided for explanatory purposes and are not limiting. As such, one or more of the acts may be omitted, one or more acts may be added, one or more acts may occur in a different order (including simultaneously with another act), etc.

At 702, an interventional instrument is navigated to a region of interest of a subject under image guidance.

At 704, an interventional action is performed with the interventional instrument at the region of interest.

At 706, an interventional action signal is generated and transmitted by the interventional instrument concurrently with the performance of the action.

At 708, an image is acquired by an imaging apparatus concurrently with the performance of the action.

At 710, a mapping between the signal and the image is determined. The mapping, in one instance, maps the location of the interventional instrument to the image acquired at the time of the interventional action.

At 712, the mapping (e.g., the location of the action) is stored in computer memory.

The methods described herein may be implemented via one or more processors executing one or more computer readable instructions encoded or embodied on computer readable storage medium which causes the one or more processors to carry out the various acts and/or other functions and/or acts. Additionally or alternatively, the one or more processors can execute instructions carried by transitory medium such as a signal or carrier wave.

An example is provided in the context of a biopsy procedure. In this example, the instrument 104 includes a biopsy needle and the imaging apparatus includes an US imaging system. The US imaging apparatus images the field of view, including the biopsy needle, when the biopsy needle is in the field of view. The images can be used to guide the biopsy needle to a biopsy site. When the biopsy (the event) is performed, the biopsy needle conveys a signal (e.g., via the transmitter 116 discussed herein and/or otherwise) that indicates the moment in time when the biopsy was performed. The US imaging system receives the signal and flags, records, etc. the image acquired at the moment in time when the biopsy was performed. This image shows the biopsy needle at the moment in time of the biopsy and hence the location of the biopsy sample at the moment in time of the biopsy.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A system, comprising:
    an interventional instrument; including:
        an interventional instrument event tracking transmitter that transmits an interventional instrument event signal in response to a predetermined interventional instrument event by interventional instrument in connection with an interventional procedure for a region of interest of a subject; and
        an actuator that invokes the tracking transmitter to transmit the signal in response to a user input; and
    an imaging apparatus, including:
        an imager that generates image of the region of interest of the subject;
        a receiver that receives the interventional instrument event signal, and
        an instrument event mapper that maps the predetermined interventional instrument event to the image based on the received interventional instrument event signal.

2. The system of claim 1, wherein the imaging apparatus includes an ultrasound imaging device and the imager includes an ultrasound transducer.

3. The system of claim 1, wherein the instrument event mapper generates the mapping at a point in time during the interventional procedure in which the predetermined interventional instrument event occurred.

4. The system of claim 1, wherein the actuator comprises a physical mechanical switch.

5. The system of claim 4, wherein the user input includes actuation of the physical mechanical switch.

6. The system of claim 5, wherein the actuation is selected from a group consisting of a push of a button, a pivot of a lever, or a slide of an element.

7. The system of claim 1, wherein the interventional instrument includes one of a biopsy needle, a guide wire, or a lumen and the interventional instrument event is a biopsy.

8. The system of claim 1, wherein the image is included in a data file, and the instrument event mapper includes the signal in the data file with the image.

9. The system of claim 1, wherein the image is included in a data file and the signal includes a time at which the interventional instrument event occurred, and the instrument event mapper includes time in the data file.

10. The system of claim 1, further comprising:
    an instrument tracking system that generates a position signal indicative of a location and orientation of the interventional instrument in the subject and conveys the position signal to the imaging apparatus, wherein the instrument event mapper maps the interventional instrument event signal to the location and orientation of the interventional instrument.

11. The system of claim 1, further comprising:
    at least a second imaging apparatus, the at least second imaging apparatus, including: a magnetic resonance imaging apparatus or a computed tomography imaging apparatus.

12. A method, comprising:
    receiving, in electronic format, a signal indicating an occurrence of an action of an interventional instrument at region of interest in a subject at a point in time during an interventional procedure;
    mapping the signal to an image acquired at the point in time during the interventional procedure in which the action occurred, generating a mapping signal; and
    storing the mapping signal in computer memory.

13. The method of claim 12, wherein the mapping includes mapping a location at which the action occurred to the image.

14. The method of claim 12, wherein the mapping identifies the image acquired at a same point in time at which the action occurred.

15. The method of claim 12, further comprising:
    incorporating the mapping signal in a data file including the image and storing the data file in the computer memory.

16. The method of claim 12, wherein the interventional instrument includes one of a biopsy needle, a guide wire, or a lumen.

17. The method of claim 16, wherein the action includes acquiring a biopsy sample.

18. The method of claim 12, further comprising:
    moving the interventional instrument to the region of interest under image guidance.

19. A system, comprising:
    means for performing an interventional procedure;

means for acquiring image data for the interventional procedure;

a receiver that receives a signal transmitted by the means for performing the interventional procedure, wherein the signal indicates a predetermined interventional procedure event occurred; and an instrument event mapper that generates a mapping between the signal and a corresponding image generated by the means for acquiring image data at a point in time during the interventional procedure in which the event occurred.

20. The system of claim 19, wherein the mapping maps the signal to a location and an orientation of the interventional instrument to the image.

\* \* \* \* \*